Jan. 19, 1971 P. L. SCOTT Plant Pat. 3,019

FELICIA PLANT

Filed Jan. 2, 1969

INVENTOR.
PAUL L. SCOTT

BY Angus & Mon
ATTORNEYS.

United States Patent Office

Plant Pat. 3,019
Patented Jan. 19, 1971

3,019
FELICIA PLANT

Paul L. Scott, Duarte, Calif., assignor to Burkard Nurseries, Inc., Pasadena, Calif., a corporation of California Filed Jan. 2, 1969, Ser. No. 788,665
Int. Cl. A01h 5/00
U.S. Cl. Plt.—68 1 Claim

ABSTRACT OF THE DISCLOSURE

A Felicia characterized by large flower heads containing rich blue ray flowers freely produced on a robust plant.

This invention relates to a new variety of Felicia plant, which plant has the botanical name polyploid *Felicia amelloides,* and is from the Compositae family and Asterae tribe. The plant ordinarily grows to a height about 48 cm. in a spread of about 75 cm. or more in a mound shape having a fairly dense sub-shrub with moderately stiff growth.

The present new or improved variety of Felicia is characterized by its large flower heads containing rich blue ray flowers freely produced on a robust plant, as set forth in the new description of the new variety.

The new variety of Felicia plants according to the present invention was developed in Duarte, Calif., and is a third generation from a seed of a "Santa Anita" Felicia from the Los Angeles County Arboretum in Arcadia, Calif. The "Santa Anita" Felicia is a tetrapolid, a sprawling plant with narrow light blue petals, originally from South Africa.

The accompanying drawings show a typical specimen of the plant according to this invention in bloom and are depicted in color as nearly true as it is reasonably possible to make the same a color photograph of this character, in which.

Figure 1:
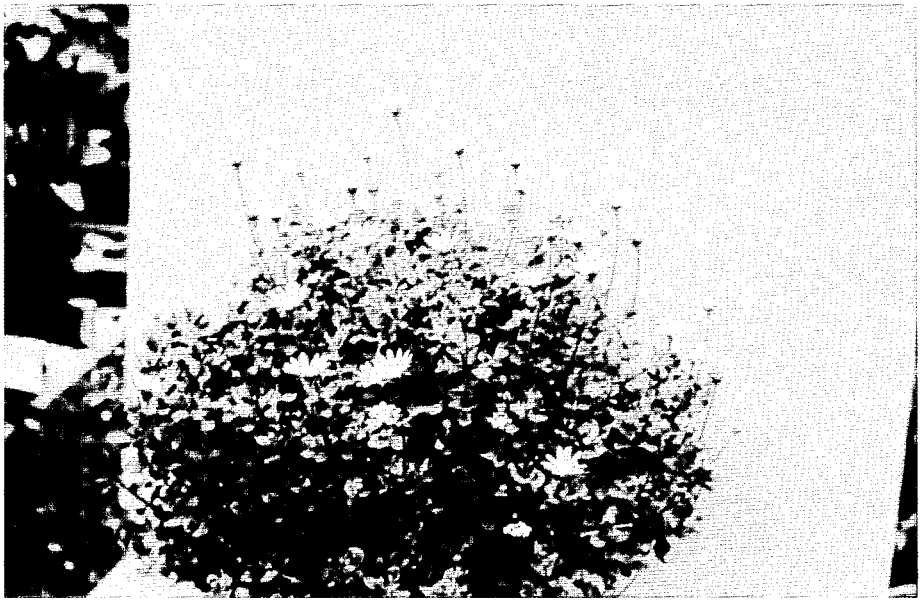
FIG. 1 is a side view of the plant in bloom.
Figure 2:
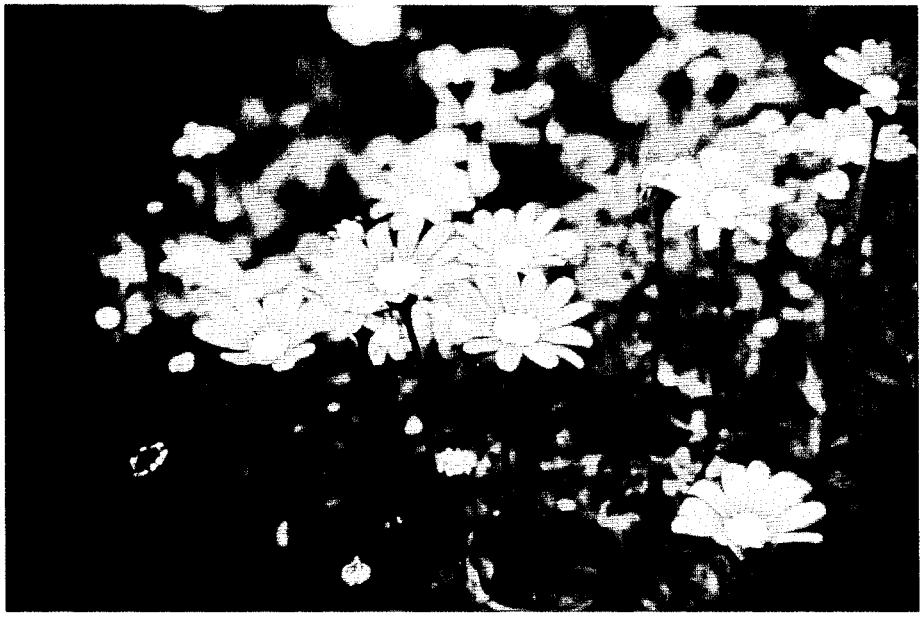
FIG. 2 is a closeup view of several heads of flowers.

Each head of the new variety of plant comprises a plurality of ray flowers disposed somewhat irregularly around a plurality of disk flowers. The ray flowers are about 13 mm. long and about 5.5 mm. wide and are elliptical in outline. When in bloom, the upper surface of the ray flowers are a substantially uniform violet-blue color, 96C on the Royal Horticultural Society (RHS) fans. The ray flowers have longitudinal veins of slightly darker color (96A RHS). The underside of the ray flowers are a substantially uniform violet-blue color (97C RHS). About thirteen ray flowers are disposed on each flower head, although that number may vary from head to head. The disk flowers each have a width of about 11 mm. and is composed of mostly sterile flowers having a yellow-orange color (14A RHS). The flower color is dependent upon nutrition and temperature range, and poor nutrition or increased temperature will make the flower petals fade sooner. The flower head has no fragrance. Each flower head lasts approximately 2 to 3 days cut and 3 to 4 days on the plant.

The buds of the plant are elongated and spheroid, the upper portion being green (143A RHS) and having spots of grayish-red (178A RHS). The lower portion of the bud is yellow green in color (144B RHS). The bud scales are puberulent and are furrowed longitudinally.

The seeds are achenes, furrowed along one edge and slightly puberulent. The seeds are ellipsoidal and about 3 mm. long and 2 mm. wide. The color of the seeds varies between black (202A RHS) and brown (200A RHS).

The involucre comprises a single row of bracts each having a diameter of about 1 mm. in a height of about 9 mm. The upper portion of the body of the bracts are green (141B RHS) having grayish-red spots (178A RHS). The lower portion of the bracts are yellow-green (144B RHS). The diameter of the involucre is about 9 mm. and its texture is puberulent. The capitula are solitary and have a width of about 3.8 cm.

The stem of the plant is green (143B RHS), tinged and minutely spotted with grayish-red spots (178A RHS). The main trunk stem diameter is about 1 cm. or more and contains internodes of about 3 cm. in length. The other stems are about 3 mm. in diameter and contain internodes of about 1.3 cm. in length. The peduncle is green (144B RHS) and is about 15 cm. long and 2 mm. thick. The peduncle is puberulent and minutely spotted with grayish-red spots (178A RHS).

The leaves are elliptic-spatulate, expetiolate, and somewhat clasping with an acute tip. The length of leaves are to about 3.5 cm. with a width to about 2.5 cm. The upper side of each leaf is green (143A RHS) and are puberulent from raised spots. The main veins are depressed and are of lighter green (143C RHS). The lower surface of the leaf is green (143B RHS), with the main veins raised. The lower surface of the leaves are puberulent with the margins entire ciliate. The foliage is in abundance.

The new and distinct plant variety has been asexually reproduced in Duarte, Calif., from cuttings of the plant. The new variety of Felicia plant is vigorous in growth and a prolific producer of blossoms. The plant produces larger flower heads of a richer blue than other varieties of Felicia and is very robust.

What is claimed is:

1. A new and distinct variety of Felicia plant substantially as herein described and illustrated, characterized as to novelty in that the flower heads contain rich blue ray flowers and are freely produced on a robust plant as compared to other varieties of Felicia.

No references cited.

ROBERT E. BAGWILL, Primary Examiner